(12) United States Patent  
Tam et al.

(10) Patent No.: US 7,322,358 B2
(45) Date of Patent: Jan. 29, 2008

(54) SOFT CLING FEMALE CONDOM

(75) Inventors: Lisa Tam, Seattle, WA (US); Glenn D. Austin, Seattle, WA (US); Yancy Seamans, Seattle, WA (US); William Robert Van Lew, Jr., Renton, WA (US)

(73) Assignee: Path, Seattle, WA (US)

( * ) Notice: Subject to any disclaimer, the term of this patent is extended or adjusted under 35 U.S.C. 154(b) by 755 days.

(21) Appl. No.: 10/665,452

(22) Filed: Sep. 19, 2003

(65) Prior Publication Data

US 2004/0107969 A1 Jun. 10, 2004

Related U.S. Application Data

(60) Provisional application No. 60/411,771, filed on Sep. 19, 2002.

(51) Int. Cl.
| | |
|---|---|
| *A61F 6/06* | (2006.01) |
| *A61F 5/37* | (2006.01) |
| *A61B 17/00* | (2006.01) |
| *A61B 19/00* | (2006.01) |
| *A61B 5/44* | (2006.01) |

(52) U.S. Cl. ................... 128/830; 128/832; 128/838; 128/884; 128/887; 128/898; 128/918; 604/347; 604/351

(58) Field of Classification Search ............... 128/830, 128/832, 836, 884, 887, 838, 898, 918, 834; 206/69; 604/347–353; 264/349; 53/429
See application file for complete search history.

(56) References Cited

U.S. PATENT DOCUMENTS

| 4,638,790 A | 1/1987 | Conway et al. |
| 4,735,621 A | 4/1988 | Hessel |
| 4,805,604 A | 2/1989 | Spery |
| 4,834,113 A | 5/1989 | Reddy |
| 4,862,901 A | 9/1989 | Green |
| 4,867,176 A * | 9/1989 | Lash ......................... 128/830 |
| 4,945,923 A | 8/1990 | Evans et al. |
| 4,976,273 A | 12/1990 | Hessel |
| 5,094,250 A | 3/1992 | Hessel |

(Continued)

OTHER PUBLICATIONS

"Who Discovered Tensegrity?", http://tensegritoy.com/Who_Discovered_Tensegrity.html, 2000.

*Primary Examiner*—Patricia Bianco
*Assistant Examiner*—Brandon Jackson
(74) *Attorney, Agent, or Firm*—Banner & Witcoff, Ltd.

(57) ABSTRACT

A female condom is provided that includes a pouch of resilient membranous material and a hydrophilic cling mechanism. According to an embodiment of the invention, the cling mechanism includes three or more foam cling elements attached to an outer surface of the pouch. Upon insertion, the foam cling elements cling lightly to vaginal walls proximate a transition zone between the vagina's introitus and its rugated internal tissue. The foam cling elements may be shaped to permit them to nestle into a user's rugated internal vaginal tissue. An inserter may be coupled to the pouch for facilitating insertion of the condom. The inserter may retain a distal portion of the pouch in a collapsed form. The cling mechanism may be contained within the dissolvable inserter. The inserter may be dissolvable in the presence of vaginal moisture. Methods are also provided for collapsing the pouch and compressing it into an insertion package.

34 Claims, 15 Drawing Sheets

U.S. PATENT DOCUMENTS

| | | | |
|---|---|---|---|
| 5,137,032 A * | 8/1992 | Harmon | 128/844 |
| 5,209,242 A * | 5/1993 | Shields et al. | 128/844 |
| 5,228,456 A | 7/1993 | Karg et al. | |
| 5,318,043 A | 6/1994 | Burr et al. | |
| 5,325,871 A * | 7/1994 | Reddy | 128/830 |
| 5,370,633 A | 12/1994 | Villalta | |
| 5,433,219 A * | 7/1995 | Spery | 128/844 |
| 5,490,519 A | 2/1996 | Hessel | |
| 5,515,862 A | 5/1996 | Artsi et al. | |
| 5,596,997 A | 1/1997 | Abadi | |
| 5,622,185 A | 4/1997 | Richardson et al. | |
| 5,623,946 A | 4/1997 | Hessel | |
| 5,687,741 A | 11/1997 | Torger | |
| 5,992,415 A | 11/1999 | Alla et al. | |
| 6,068,899 A * | 5/2000 | Osborn et al. | 428/35.2 |
| 6,170,484 B1 * | 1/2001 | Feng | 128/830 |
| 6,341,607 B1 | 1/2002 | Couvrear | |
| 6,520,922 B2 | 2/2003 | Michelle | |
| 6,569,083 B1 | 5/2003 | Kassman | |
| 2002/0038658 A1 | 4/2002 | Austin et al. | |

* cited by examiner

SOFT CLING FEMALE CONDOM

This application claims priority to co-pending U.S. provisional application Ser. No. 60/411,771, entitled "SOFT CLING FEMALE CONDOM," which was filed on Sep. 19, 2002, the content of which is hereby fully incorporated by reference.

FEDERALLY SPONSORED RESEARCH AND DEVELOPMENT

This invention was made in part with government support under Cooperative Agreement No. DPE-5968-A-00-0025-00 awarded by the Agency for International Development. The U.S. Government has certain rights in this invention.

TECHNICAL FIELD

The present invention relates to barrier methods of human contraception and prevention of sexually transmitted diseases (STDs). More specifically, the invention relates to female condoms, i.e., condoms worn by a woman or otherwise used in a passive sexual organ such as the vagina or anus.

BACKGROUND OF THE INVENTION

Unintended pregnancy and STDs present serious health and social consequences for individuals and society at large. Known prevention and protection measures have reduced these problems to some extent. Male condoms are a well-known form of a barrier device that provide varying degrees of protection against unintended pregnancy and STDs. Male condoms, however, generally require the male partner to initiate use after an erection has been attained, thus frequently causing an awkward disruption of intimacy and foreplay. Additionally, many women would prefer not to have to rely on their male partner to provide their protection. Male condoms are disliked for a variety of additional reasons, including reduced sensation for the male partner.

Problems associated with male condoms have led to the development of various forms of female condoms that a woman can pre-place in her vagina before intercourse. Unlike a conventional diaphragm or cervical cap, which covers only a region of the vagina near the cervix or the cervix itself, known female condoms generally provide a tubular receptacle extending along the length of the vaginal canal and extending over all or some of the genitals, thereby fully encompassing an inserted penis and affording increased protection. Such devices advantageously empower a woman to protect herself from unintended pregnancy and STDs, without reliance on the male partner.

While known female condoms provide a level of protection and advantage over conventional male condoms, they do not present an ideal solution. Several problems can be identified. Some female condoms are difficult to use and others may be uncomfortable for some women. Both of these problems may reduce the pleasure of intercourse for both the male and the female partner. With many designs, the outside portion of the female condom may shift and twist excessively prior to and during initiation of intercourse. This may require the woman to hold the outside portion with one or both hands during penis insertion, which can be disruptive and awkward. A related problem of known female condoms is a lack of stability of the condom within the vaginal canal. The condoms may move around, and fall partially out, or a portion intended to remain outside of the vagina may be pushed inside. This lack of stability compromises barrier protection, and may make both partners feel nervous and insecure during intercourse. The movement of the pouch with the penis also decreases sensation of the male partner.

Hessel U.S. Pat. Nos. 5,490,519 and 5,623,946 disclose tubular devices worn by a female for protection against transfer of infectious matter during sexual intercourse. This general type of condom is available commercially as the REALITY condom. These tubular devices have an open end defined by a first ring, and a second closed end to be positioned at the distal end of the vagina. The internal tubular portion of the condom is designed to be retained by retaining means positioned at the closed end, e.g., a second ring. The second ring is oriented at an acute angle relative to first ring, and is designed to wedge or anchor around the cervix in a manner similar to a diaphragm. In use, this ring may slip away from its anchor point and permit a portion of the front part of the condom to hang or dangle outside of the woman user. Also, because the retaining means acts at the distal end of the vagina, security of the first (outer) ring is dependent on the length of the vaginal canal.

Evans et al. U.S. Pat. No. 4,945,923 also discloses a tubular contraceptive device to be worn by a woman. The device includes an outer ring and an inner ring positioned at a closed distal end of the device. The inner ring, like the Hessel devices, is designed to anchor the bottom end of the device around the cervix of a user. It is similarly susceptible to slippage from its cervical anchor point, and twisting or displacement during use.

Another type of female condom is commercially available, which is known as the V'Amore condom. The V'Amore condom is manufactured in India and has a design generally similar to the REALITY condom. An outer (proximal) ring of the V'Amore condom is shield-shaped, and retention of an inner pouch is provided by a sponge that is intended to lodge somewhere in the distal region of the vagina near the cervix. The V'Amore condom likewise may lack stability within the vaginal cavity, and does not assure close stable positioning of the outer shield.

Another known type of female contraceptive device is known as a panty condom. While providing external stability, these devices do not adequately address the need for stability of the condom pouch within the vagina. A pouch portion of the panty condom is inserted into the vagina, which may pull inside out, or twist or turn. This can adversely affect male partner sensation and compromise barrier protection. Additionally, with known panty condoms, air tends to be pumped into the vaginal cavity during intercourse. This can be noisy and uncomfortable for the woman. After intercourse, the devices may turn inside out during withdrawal, thereby making a mess and increasing the potential for disease transmission and unintended pregnancy. Additionally, the panty configuration may be objectionable to users for aesthetic reasons.

Artsi et al. U.S. Pat. No. 5,515,862 discloses a female condom generally similar to the aforementioned panty arrangement. The device has an extensive external shield, which is adhesively applied to cover pubic, abdominal, groin, thigh and anal regions, and a flexible tube extending from the shield to a closed end. Multiple rings are positioned along the length of the tube. One ring is used at the closed end to anchor around the cervix, similar to a diaphragm, and additional rings placed along the length of the tube are intended to lodge against the muscular tissue of the vaginal passage, to prevent slippage of the tube along the length of the vagina during use. The disclosed "semi-rigid" intermediate rings may to some extent improve stability of the tube in the vagina canal, yet no guidance is provided with respect to a positioning, sizing or configuration of the intermediate rings to maximize internal/external condom stability. Additionally, multiple rings positioned along the length of the condom may be encountered by a man's penis during intercourse, thus causing discomfort to the male partner.

Commonly assigned co-pending U.S. application Ser. No. 09/921,016, published under No. US-2002-0038658-A1 on Apr. 4, 2002 (the '658 application), discloses "tensegrity" based female condom designs. The disclosure of that application is incorporated herein by reference. According to aspects of the '658 application, tensegrity-based female condoms employ compression and tension forces to provide substantial stability of the female condom. As such, when a tensegrity-based condom is inserted into a woman's vagina, the woman's introitus acts on a proximal section of an elongated pouch extending between internal and external biasing members (e.g., rings) of the condom. Inward compressive forces exerted by the introitus on the inner ring of the condom cause the inner ring to be pushed distally within the vaginal canal, and the proximal pouch section to become a tension member pulling against the external ring. This causes a "tenting" of the proximal pouch section against the introitus.

Tensegrity-based female condoms can provide a high degree of internal and external stability; however, the degree of stability may vary depending on the depth of tissue of the user's introitus. In other words, the degree of stability may vary for different sizes of women.

The '658 application further discloses an embodiment of a tensegrity-based female condom that includes pads of resilient material, such as foam, that form an internal biasing member of the condom. The pads may be placed on the outside of pouch material and may be made of hydrophilic polyurethane, which provides mucosal cling to the user's vaginal walls. The mucosal cling acts to increase stability of the female condom, and/or reduce reliance on the spring action of the pad material (i.e., internal biasing member) to maintain the intermediate section of the pouch expanded against a distal portion of the introitus. Thus, hydrophilic pads act in concert with the tensegrity principle to provide condom stability. Depending on its size, a tensegrity-based female condom is applicable to women having an introitus' depth within a given range.

SUMMARY OF THE INVENTION

Addressing the above-described issues and other issues that will become apparent when reading this specification, aspects of the present invention provide a female condom that can engage vaginal mucosa at different depths within a user's vagina. According to an embodiment of the invention, a female condom includes a pouch of resilient membranous material and a cling mechanism. The cling mechanism is adapted to cling lightly to walls of a vagina proximate a transition zone between the vagina's introitus and its rugated internal vaginal tissue for anchoring the pouch in or slightly beyond the vagina's introitus. In embodiments of the invention, the cling mechanism adheres to the pouch without imparting outward biasing force thereto. According to aspects of the invention, the cling mechanism may include hydrophilic foam. The hydrophilic foam may have a variety of shapes that can permit the foam to nestle into a user's rugated vaginal tissue.

Further aspects of the invention provide an insertion cap at the closed end of the pouch, which serves to contain a distal portion of the pouch until insertion into the user's vagina. Other aspects provide a dissolvable inserter, which dissolves in the presence of vaginal moisture. In alternate embodiments, the cling mechanism may be contained in the insertion cap or dissolvable inserter prior to insertion into the user's vagina. According to further aspects, methods for collapsing the pouch and compressing it for easy insertion are provided. Other features and advantages of various aspects of the invention will become apparent with reference to the following detailed description and figures.

BRIEF DESCRIPTION OF THE DRAWINGS

The invention will be described in detail in the following description of preferred embodiments with reference to the following figures wherein.

DETAILED DESCRIPTION OF THE INVENTION

Figure 2:
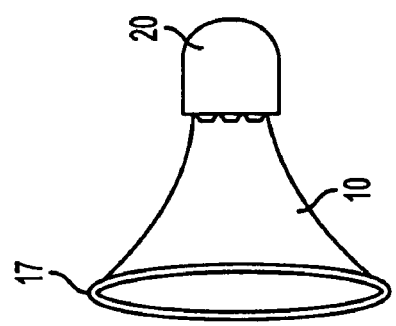
FIG. 2 is an elevational view of the female condom of FIG. 1 in a collapsed form.
Figure 1:
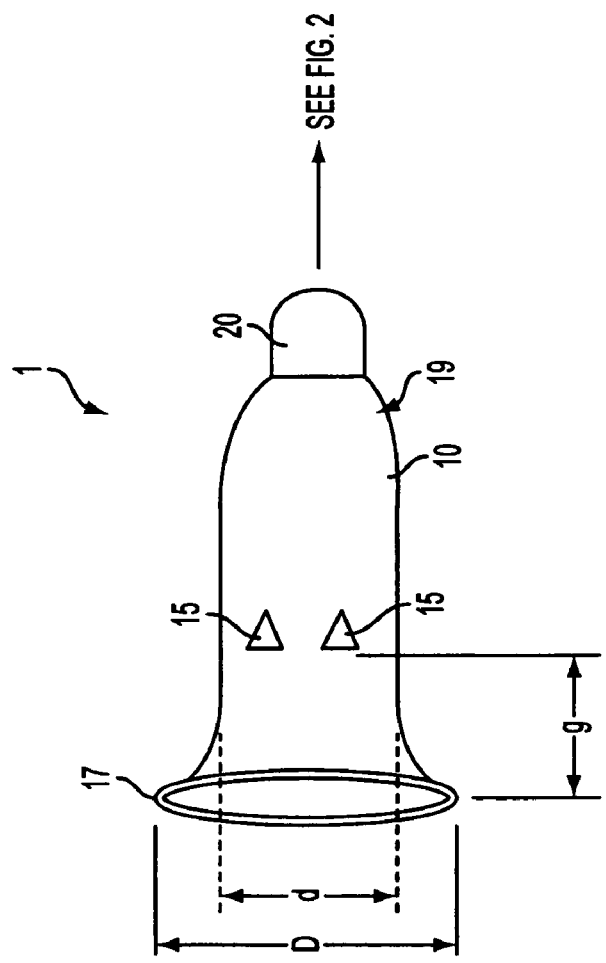
FIG. 1 is an elevational view of a female condom in an expanded form according to an embodiment of the invention.

The various aspects of the invention may be embodied in various forms. The following description of the figures shows by way of illustration various embodiments in which aspects of the invention may be practiced. It is to be understood that other embodiments may be utilized and structural and functional modifications may be made without departing from the scope of the present invention. Referring now to FIGS. 1 and 2, a female condom 1 according to an embodiment of the invention is shown. As shown, female condom 1 includes an elongated tubular pouch 10 of thin membranous material, cling elements 15, an outer ring 17, and an insertion device 20. FIG. 1 shows female condom 1 in an expanded form, and FIG. 2 shows female condom 1 in a collapsed form. In the expanded form, a distal end portion of pouch 10 may be disposed within insertion device 20.

Pouch 10 is generally a tubular receptacle, which extends along the length of a vaginal canal during use. Outer ring 17 is a resilient ring secured about the open end of pouch 10. Outer ring 17 is sized such that, in use, it remains disposed external, generally contacting the region surrounding the vaginal opening (the vulva), and the perineum of the female user. Outer ring 17 and pouch 10 may be made from the same or a compatible elastomeric material, such as a urethane, polyolefin, latex, silicone or thermoplastic elastomer. For example, outer ring 17 material may be made from ESTANE 58810 or 58887 (available from B.F. Goodrich of Cleveland, Ohio).

Cling elements 15 are disposed at an intermediate portion of pouch 10 along its outer surface. Pouch 10 may be made of urethane or like materials. For example, it may be made from 1 mil blown film extruded urethane, which is available from Stevens Urethane of Holyoke, Mass. In a preferred embodiment, pouch 10 is made of urethane having an average thickness between approximately 0.00075 inches and approximately 0.004 inches or more preferably approximately 0.0012 inch. The spacing between outer ring 17 and cling elements 15 is shown as gate length g, which may be between approximately three inches and approximately four inches, and is more preferably approximately 3.5 inches. The diameter d of pouch 10 at the position of cling element 15 may be between approximately 1.5 and 2 inches, and preferably approximately 1.85 inches and the diameter of outer ring 17 may be between approximately 1.5 and 6 inches, preferably approximately 3.15 inches. Alternatively, Pouch 10 may be made of dipped urethane, such as 0.018 inch thick dipped HT-8 urethane, or HT-3 or HT-13 (available from Apex Medical Technologies of San Diego, Calif.).

In a preferred embodiment, cling elements 15 include a one or more thin foam segments 15 placed at gate length g from outer ring 17 for anchoring pouch 10 in or slightly beyond the user's introitus. Foam segments 15 are made from soft hydrophilic foam, which provides mucosal cling. Foam segments 15 preferably have a thickness of between approximately 0.03125 and 0.25 inches, and more preferably between approximately 0.0625 and 0.125 inches. Preferably, two to eight foam segments are used, more preferably four to six foam segments are used, and most preferably four segments are used. Alternatively, cling elements may be applied as a coating in liquid or in semi-liquid form.

The foam used for foam segments 15 may include an open cell urethane foam material, which is often used for wound dressing. For example, AVITAR HYDRASORB medical grade polyurethane hydrophilic foam (available from Avitar, Inc. of Canton, Mass.) may be used to form foam segments 15. Urethane foam is preferred due to its melt-compatibility with the urethane pouch of the present invention, enabling the welding of the foam to the pouch without the use of an adhesive. In alternate embodiments, the foam may be any biocompatible hydrophilic foam, such as the hydrophilic foam available from Rynel (Rynel Ltd., Route 27, Boothbay, Me. 04537). As discussed above, this foam layer may be effective in thicknesses ranging from between approximately 0.03125 and 0.25 inches, and more preferably between approximately 0.0625 and 0.125 inches. Best results have been obtained with the foam placed in a number of discrete shapes on the surface of the female condom pouch in a belt-like pattern that places the foam at or inside the transition zone between the introitus and the rugated internal vaginal tissue. The application of 4-6 shapes is preferred with an average total surface area between approximately 0.4 and 2.25 $in^2$, and most preferably approximately 0.75 $in^2$. A most preferred embodiment may include four shapes each with an average surface area of approximately 0.1875 $in^2$.

The foam segments 15 shown in FIG. 1 may include HYDRASORB foam approximately 0.0625 inches thick, and formed into four triangle shaped segments 15, with a base length and height measuring approximately 0.75 inches×0.375 inches (two segments shown). The geometry and area of these shapes can be varied. In general, the shape of foam elements 15 allows for efficient packaging into the insertion capsule and enables them to nestle into the rugated vaginal disuse to increase device stability. The shapes may be circles, ellipses, obrounds, triangles, or other shapes as would be known to one skilled in the relevant art. As discussed below with female condom 1', an elliptical shape is preferred as it may engage (nest) better than other shapes within the rugated internal vaginal tissue. The foam shapes 15 are preferably laminated to a melt-compatible urethane film, such as the urethane film used to produce pouch 10 to allow easier and more secure welding of foam shapes 15 to pouch 10.

In a preferred embodiment, female condom 1 includes an insertion device 20. In the embodiment shown in FIGS. 1 and 2, insertion device 20 includes a foam cap (nose cone) 20 attached to the closed end of pouch 10. Cap 20 may be approximately one inch long and approximately one inch in diameter. The distal portion 19 of pouch 10 and foam segments 15 are packed inside the cap for handling during insertion. The cap releases the foam shapes after insertion. Foam cap 20 may be made from a foam material similar to that of foam cling elements 15, and may be made from an open cell urethane foam material, such as ⅛ inch AVITAR HYDRASORB or 2.4 mm RYNEL 562-B (available from Rynel, Inc. of Boothbay, Me.).

In an alternate embodiment, insertion device 20 may be made of a biocompatible dissolving material such as polyvinyl alcohol (PVA/PVOH). Inserter 20 is preferably formed into a spherical, envelope-shaped or bullet-tipped cylindrical shape to facilitate insertion; although, the capsule could be made of any other suitable shape as would be known to one skilled in the relevant art. In alternate embodiments, the dissolving material may be gelatin, hydropropylmethyl cellulose (HPMC), steric acid, or any compatible material which displays the desired dissolution rate, as would be known to one skilled in the relevant art. Inserter 20 may be made through dipping or through fabrication to allow for optimization of the cap wall thickness in order to optimize the dissolution time and minimize residual material after use of the condom. In a preferred embodiment, the dissolution time is between approximately 20 and 120 seconds, and more preferably between approximately 30 and 60 seconds.

In the embodiment shown in FIGS. 1 and 2, foam cap 20 holds foam elements 15 and pouch 10 secure for manual insertion. This design eliminates the need for an external insertion aid (e.g., tube-type inserter similar to that used for tampons)—foam cap 20 takes the place of the inserter tube. This reduces the number of condom components and decreases cost. It may also increase acceptability of the device, as tampons with inserters are not used in some countries. Further, insertion is facilitated and made more comfortable. The foam cap is generally easier to handle than a plastic inserter. It is also softer and more compact.

Female condom 1 may rely on slight distension from foam cap 20, which could provide additional condom retention. Cling elements 15 provide a surface treatment or mechanism on the vaginal side of the condom pouch that provides cling or light adhesion against the vaginal mucosa. In addition to adhesion, surface features may be used, which lodge in the rugated tissue of the vaginal walls. The cling force need only be stronger than the pull-out forces created by withdrawal of the penis during sex. If the penile surface of the condom is highly lubricious, the need for cling on the vaginal mucosa is reduced. The cling force should exceed the pull-out forces created by withdrawal of the penis during sex in order for the condom to remain stable and maintain comfort, sensation, safety and effectiveness.

Unlike the internal biasing member of tensegrity-based condoms, the foam cling shapes can engage the vaginal mucosa at many different depths within the vagina, even within the introitus itself. This permits a single "size" of device to fit a much broader range of women than a tensegrity-based condom. As shown in FIG. 1, thin foam segments 15 are preferably placed at approximately a three to four inch gate, g, for anchoring in or slightly beyond the introitus of most women.

As also shown in FIG. 1, the distal portion of the condom is preferably packaged in a collapsed, compressed state. As discussed later, the pattern of collapsing and compressing is important to stability during handling and insertion of the device and in functional deployment of the device within the vagina. The collapsed and compressed portion of pouch 10 is held together by cap 20, which aids insertion. For example, cap 20 may be inserted into the vagina much like an OB ("applicator-less") tampon. After initial insertion, condom 1 can be placed into its final position with a finger or penis. Cling elements 15 are then released from their collapsed/compressed state by pushing the cap beyond the cling elements and into contact with the vaginal mucosa where they absorb a small amount of fluid and cling lightly. In particular, as cap 20 is pushed further into the user's vagina, the foam cling elements escape (deploy) from within the open skirt-like end of cap 20 to come in contact with the vaginal walls. The shaped foam elements 15 may also lodge in the user's vaginal rogations. The cling and/or lodging provides an anchor for pouch 10 within the user's vagina. The internal portion of condom pouch 10 may be in tensegrity balance with outer ring 17, but this is not required. If tensegrity balanced tension is not established, outer ring 17 may hang slightly away from the woman's body, but can still function to hold the open end open, flat, and properly positioned over the opening to the user's vagina.

Unlike tensegrity-based condoms, there is no "active" insertion feature (e.g., internal biasing member) inherently built into soft cling condoms 1. The collapsed/compressed portion of pouch 10 is preferably contained in a form that makes it easy to grasp and insert to its functional depth within the user's vagina. As shown in FIG. 2, this may be accomplished by compressing distal portion 19 inside cap 20. Cap 20 is preferably made from a foam material similar to that of the foam shapes of cling elements 15, or alternatively a different soft elastomeric material. Cap 20 is secured to the closed end of condom pouch 10, and serves to contain the distal end 19 of pouch 10 and foam cling elements 15 for insertion and initial deployment.

Figure 4:
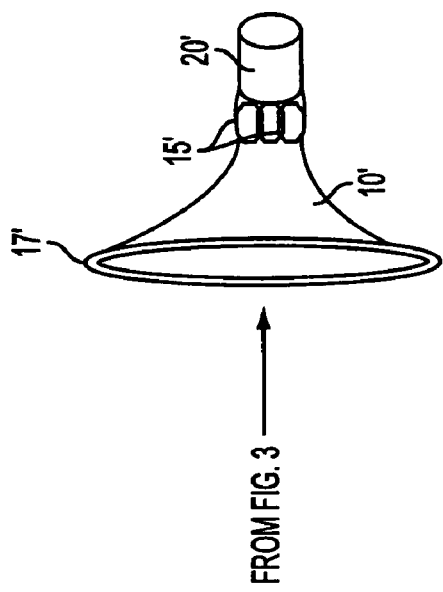
FIG. 4 is an elevational view of the female condom of FIG. 3 in a collapsed form.
Figure 3:
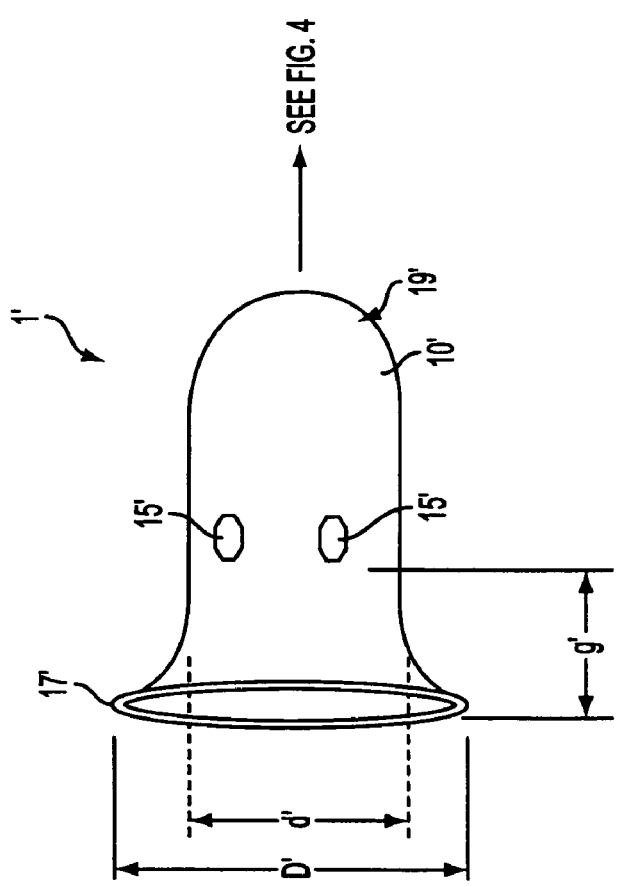
FIG. 3 is an elevational view of a female condom in an expanded form according to another embodiment of the invention.

Referring now to FIGS. 3 and 4, a female condom 1' is shown according to another embodiment of the invention. FIG. 3 shows female condom 1 in an expanded form, and FIG. 4 shows female condom 1 in collapsed form. Female condom 1' generally includes the aspects and preferences of female condom 1, except as discussed below. As shown, female condom 1' includes a pouch 10', an outer ring 17', and cling elements 15'.

Foam elements 15' retention material are generally lozenge-shaped foam segments and may have pinched (compressed) circumferential edges, and preferably have dimensions of approximately 0.75 inches×0.375 inches. Foam elements 15' may be made from hydrophilic polyurethane foam having thicknesses of between approximately 0.03125 and 0.25 inches, and more preferably between approximately 0.0625 and 0.125 inches, as discussed above with regard to foam elements 15.

Figure 5:
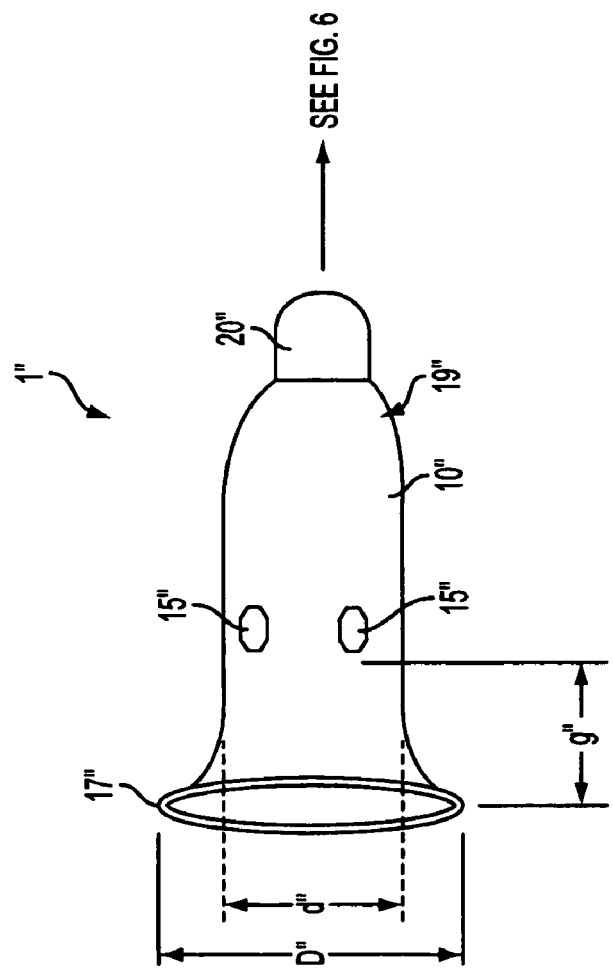
FIG. 5 is an elevational view of a female condom in an expanded form according to a further embodiment of the invention.

To provide an insertion device, a distal portion 19' of pouch 10' is contained in a dissolving band 20' (or cap structure 20 as described above) made of a safe material that first weakens, then dissolves in the presence of vaginal moisture, thus releasing the foam shapes for cling/adhesion to the vaginal walls. Distal portion 19' may be coupled to dissolving band 20' by slidably inserting distal portion 19' into dissolving band 20'. A preferred material for dissolving band 20' is polyvinyl alcohol (PVA), similar to that used for contraceptive film. As shown in FIG. 5, the distal end 19' of pouch 10' is compressed and held with a strip of vaginal contraceptive film 20' containing a water-soluble polymer, such as the preferred material polyvinyl alcohol. The strip of vaginal contraceptive film 20' is preferably approximately 0.5 to 1.75 inches in length, and more preferably about 1 to 1.75 inches in length. As discussed above with cap 20, insertion of condom 1' with contraceptive film 20' is similar to an OB tampon. In another embodiment, a capsule open at one or both ends (not shown) composed of the same water soluble polymer may also be used as an insertion device.

The thin foam segments have been proven to anchor sufficiently for use. Small rounded elliptical (lozenge) shaped elements as shown may engage (nest) better than other shapes within rugated internal vaginal tissue. Diamond, triangular and tear drop shapes may also be used. The elliptical shaped elements allow for efficient packaging into the insertion capsule. The compact and rounded geometry enables the elliptical shapes to nestle into the rugated vaginal tissue to increase device stability. In alternate embodiments, the shapes may be circles, obrounds, triangles, or other shapes as would be known to one skilled in the relevant art.

For insertion, the distal end 19' of pouch 10' is held by the illustrated dissolving band 20' in a neat pellet shape. The band 20' may or may not contain the foam cling elements 15' as it may be desirable for the foam elements to aid in providing initial insertion cling during initial placement. The pellet is held and inserted into the vagina, similar to an OB tampon. By replacing foam cap 20 with a dissolving band 20', insertion and deployment may become more uniform. The dissolving nature of band 20' implies (and thus aids in indicating) an intended single use nature of the device. By reducing the overall size of the device, user acceptability may be increased.

Figure 6:
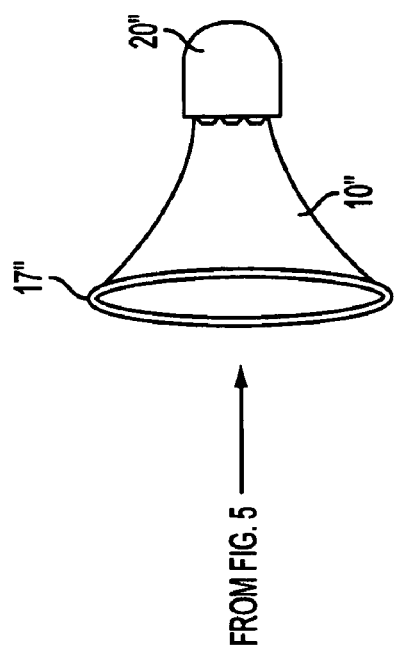
FIG. 6 is an elevational view of the female condom of FIG. 5 in a collapsed form.

Referring now to FIGS. 5 and 6, a female condom 1" is shown according to another embodiment of the invention. FIG. 5 shows female condom 1" expanded, and FIG. 6 shows female condom 1" in collapsed form prior to insertion. Female condom 1" generally includes the aspects and preferences of female condom 1, except as discussed below. As shown, female condom 1" includes a pouch 10", an outer ring 17", cling elements 15", and insertion device 20". Pouch 10" is preferably made of standard 1 mil blown film extruded urethane, and preferably has a thickness of about 0.0012", but may include other materials as discussed above with condoms 1 and 1'. Gate length g' is preferably between approximately 3 and 4 inches, and is more preferably approximately 3.5 inches.

Cling elements 15" retention material are each preferably ⅛ inch HYDRASORB foam, die cut ⅝ inch 30° ellipses with pinched (compressed) circumferential edges. Insertion device 20" may be made of 0.063 inch RYNEL 562-6 foam, die cut and welded to pouch 10", having dimensions of approximately 11 inch diameter×1 inch length. The distal portion 19" of pouch 10" and the foam segments 15" are packed inside the cap 20" for handling during insertion. The cap 20" should release the foam elements 15" and distal portion 19" after insertion.

Female condom 1" is a generally more refined design than female condom 1. Foam components 15" are die cut and welded to pouch 10". This serves to make cap 20" and shapes uniform while also reducing fabrication time. Foam cap 20" is also die cut and welded with a heated die. Foam cling elements 15" are preferably cut from ⅛ inch HYDRASORB foam. The shapes look significantly thinner because of pinching on the edges that results from die cutting. When welded onto pouch 10", foam elements 15" are intended to appear highly integrated with pouch 10" for aesthetic purposes.

Foam cap 20" was developed to replace the plastic inserters used with previous capless foam cling designs. As has been described, cap 20" holds foam elements 15" and pouch 10" secure for manual insertion. The weld strength may be increased by expanding the area of the weld and by skinning and compressing the foam at the weld. The area of the weld is roughly ¼-⅔, and is preferably between approximately ¼ and ½ of the internal cap area from the tip to the open end so as to leave space for the foam shapes and pleats of pouch material.

Various methods can be employed for collapsing and compressing the pouch for easy insertion. In one embodiment, folds and pleats should be formed, and wadding and compression should be done, in a manner that permits the condom pouch to open (deploy) easily and uniformly when pushed inward by a finger or penis. Methods have been derived for folding that employs negative air pressure to create and hold small pleats in the surface of the condom. These pleats are then collapsed while negative air pressure is maintained to avoid cul-de-sacs, twists, or fold-backs that might prevent easy deployment. Apparatus usable for these exemplary methods are illustrated in the FIGS. 7-19.

Figure 7:
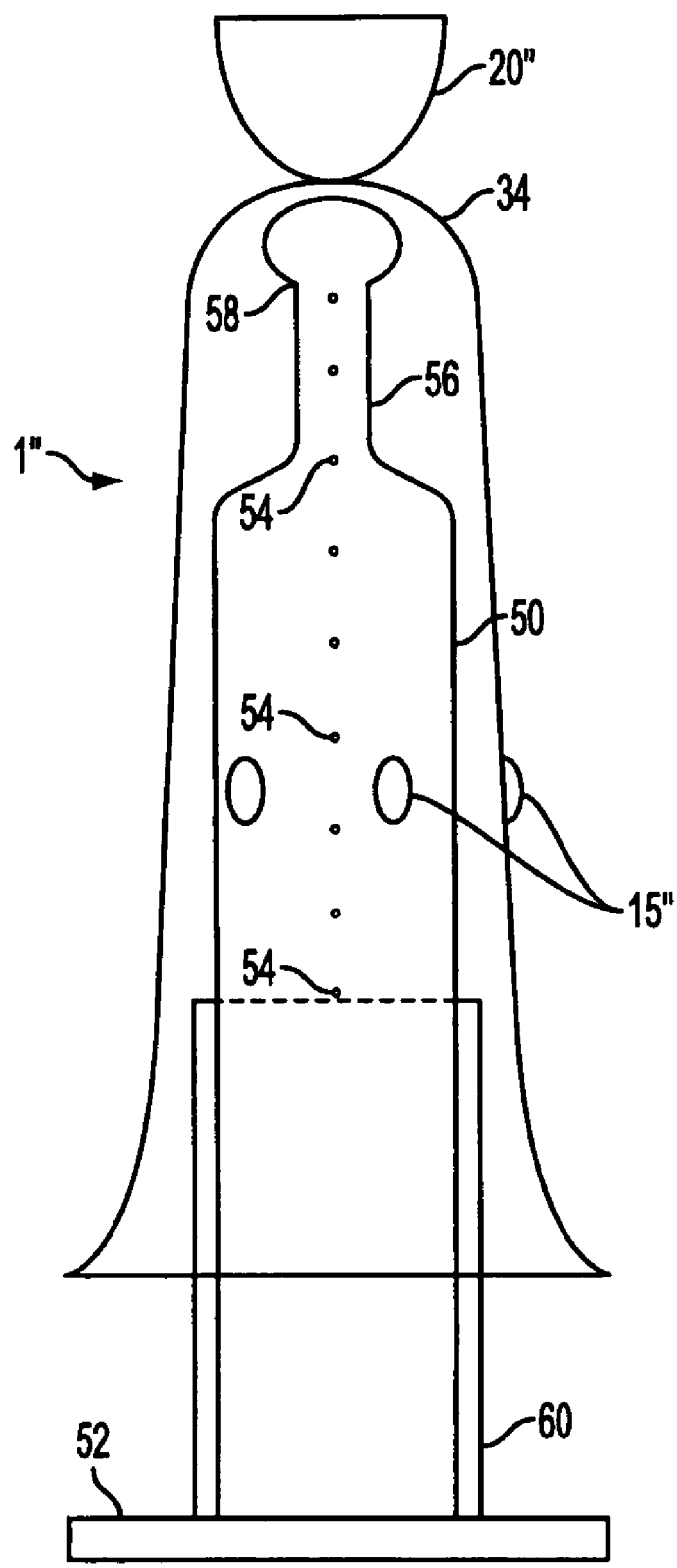
FIG. 7 is an elevational view of a female condom disposed on a mandrel for packaging the condom according to an embodiment of the invention.
Figure 8:
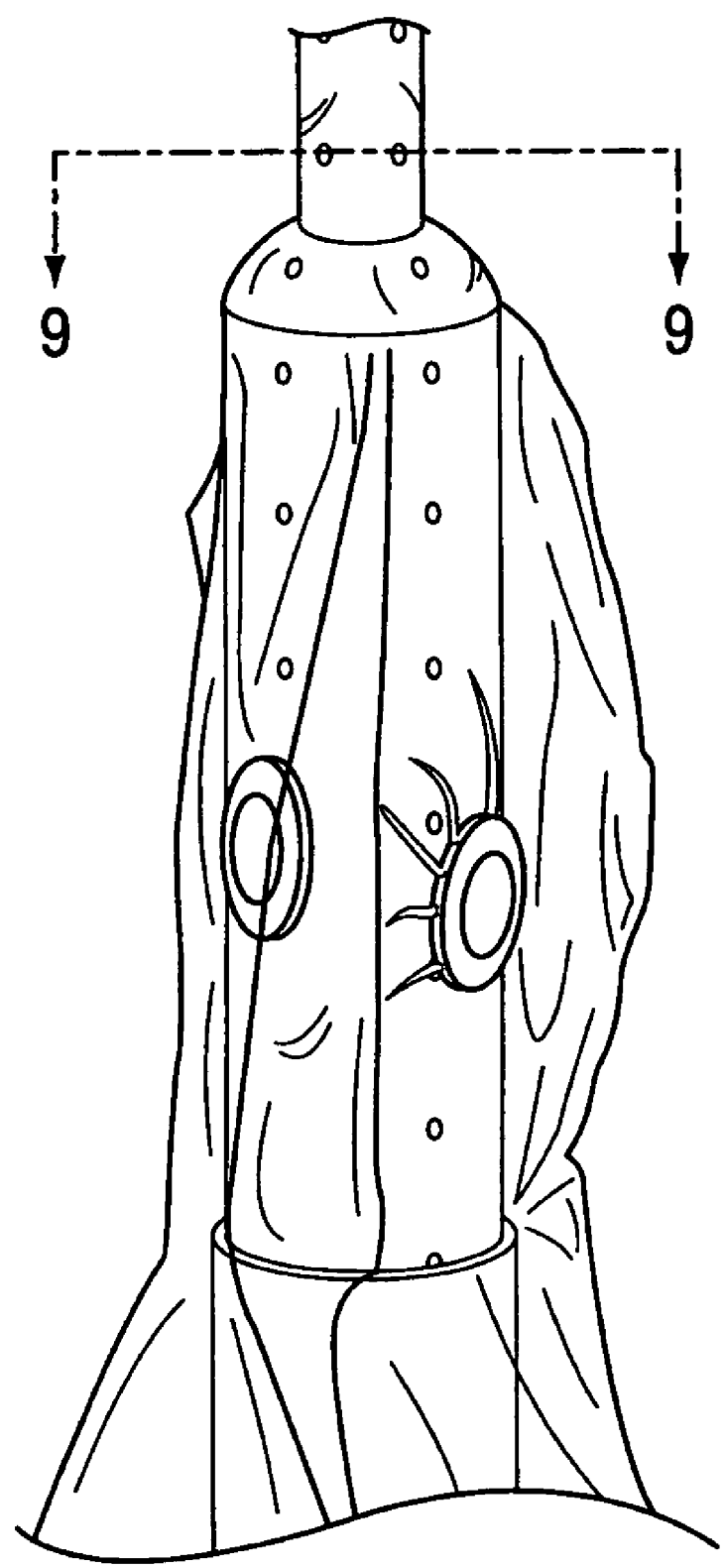
FIG. 8 is a close-up elevational view of an intermediate portion of the female condom of FIG. 7 with vertical pleats formed according to the embodiment of FIG. 7.
Figure 9:
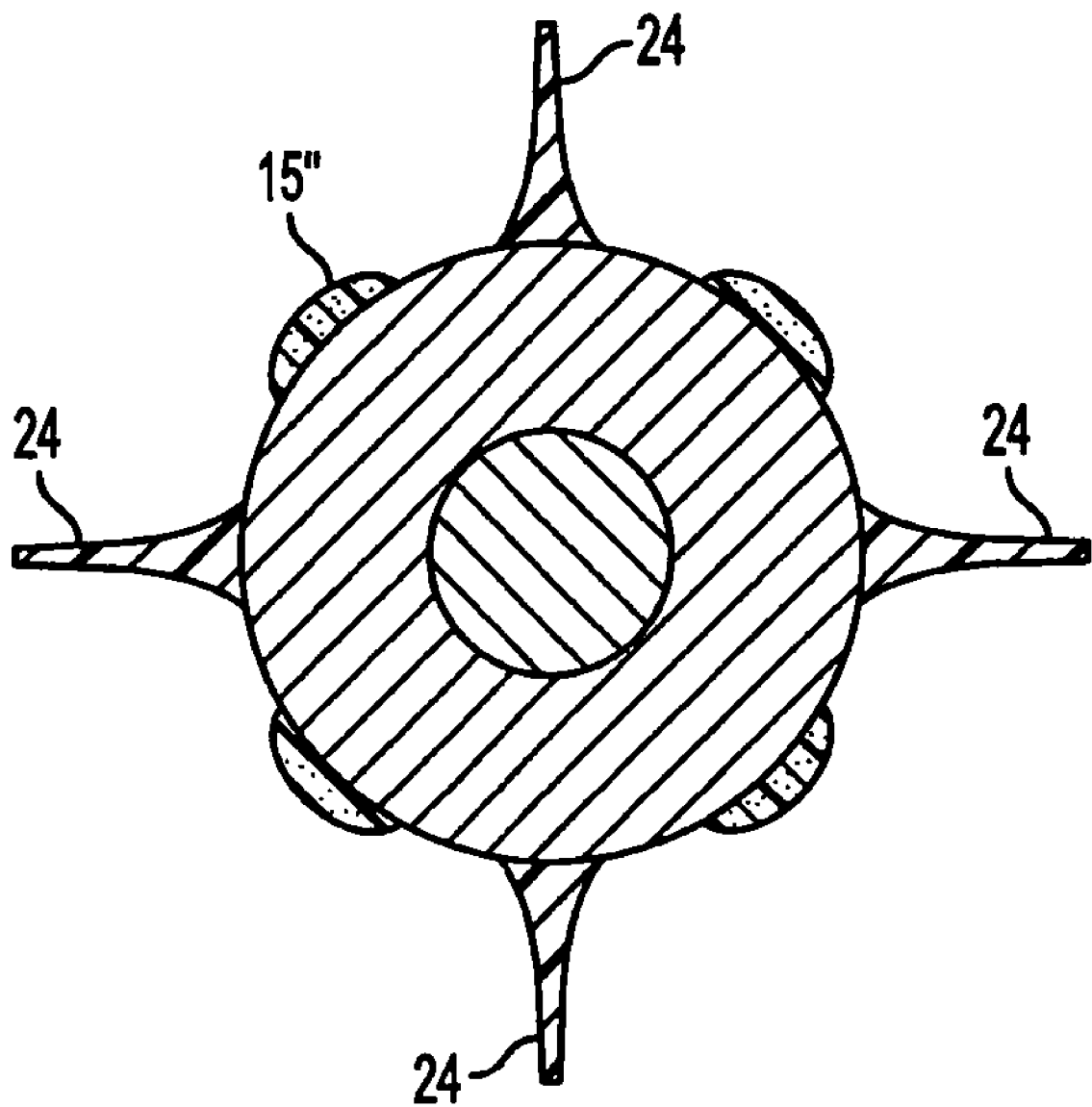
FIG. 9 is a cross-sectional view through the female condom with vertical pleats of FIG. 8 at the neck portion of the mandrel shown in FIG. 7.
Figure 10:
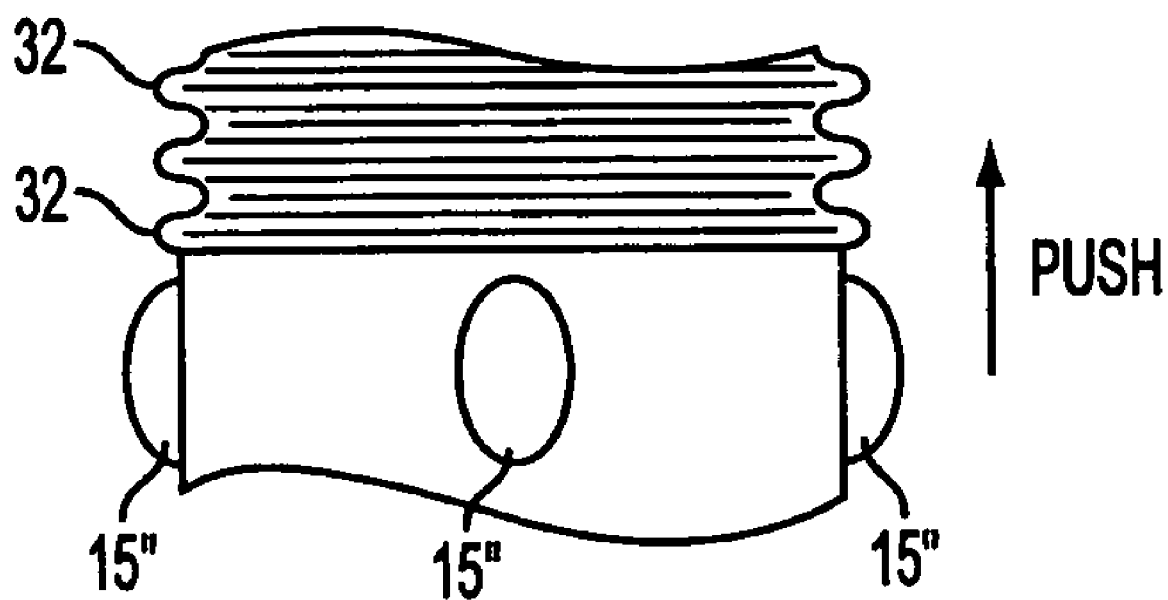
FIG. 10 illustrates compressing the female condom of FIG. 8.

Referring now to FIGS. 7-11, a method for collapsing and compressing the pouch of female condom, such as female condom 1", is generally shown. As shown in FIGS. 8 and 9, the present pattern first induces 4 or more longitudinal pleats 24 generally parallel to the long axis of condom pouch 1". As shown in FIG. 10, it then induces a large number (approximately 15-40) of circumferential pleats 32, generally perpendicular to the long axis, from foam shapes 15" to the distal tip 34 of pouch 10". This organization of the pouch material and foam shapes permits compact storage and smooth deployment. Current methods of inducing these pleats 24 include use of a cylindrical male mandrel 50 equipped with vacuum (negative pressure) to hold pleats 24 in a tightly closed position as they are being collapsed. This collapsed and compressed portion of pouch 10" is held together by a band or cap structure 20" that aids insertion as discussed above.

As shown in FIGS. 7 and 8, a hollow mandrel 50 having an outer surface of lubricious plastic or the like is supported on a base 52 that permits attachment of a vacuum source via tubing 51. The mandrel 50 is sized to extend within and generally along the length of the female condom 1". Other embodiments, such as 1 and 1', could also be compressed using this method and mandrel 50. Arrayed on the cylindrical surface of mandrel 50 are a plurality of holes 54 communicating with the hollow mandrel interior. Although not shown, one or more holes 54 could be formed in the tip of the upper end 56 of mandrel 50. A vacuum developed within the mandrel interior causes the condom material to cling to mandrel 50 and form pleats 24 as shown in FIGS. 8 and 9. The upper end 56 of mandrel 50 may be necked down, generally similar to the neck of a wine bottle, and a lip 58 may be formed near the top of the upper end 56. A cylindrical sleeve 60 is mounted on, and slidable along, the main (large diameter) portion of mandrel 50, to act as a vacuum valve serving to selectively close-off the arrayed vacuum holes 54 formed in the cylindrical mandrel walls.

Figure 11:
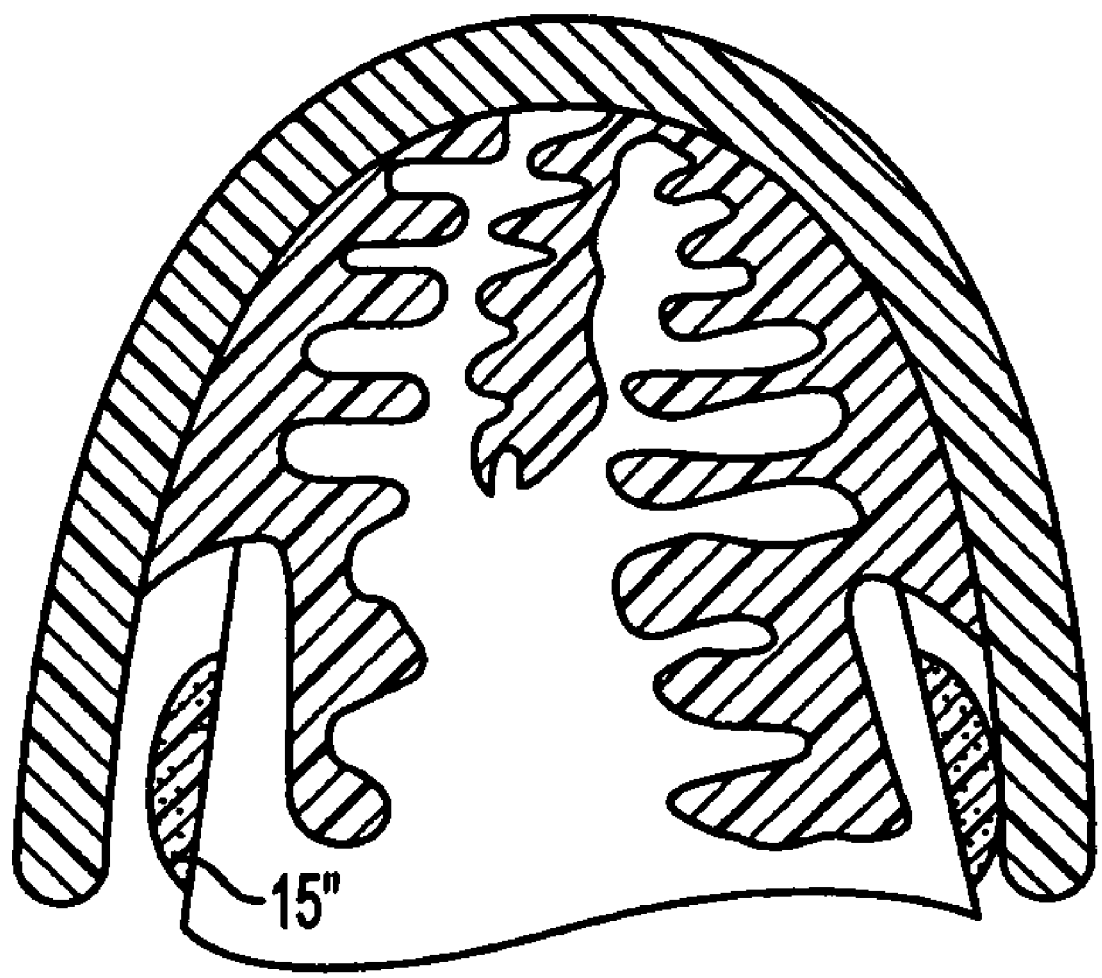
FIG. 11 is a cross-sectional view of cap 20" shown in FIG. 7 with the female condom in a collapsed form according to the embodiment of FIG. 7.
Figure 12:
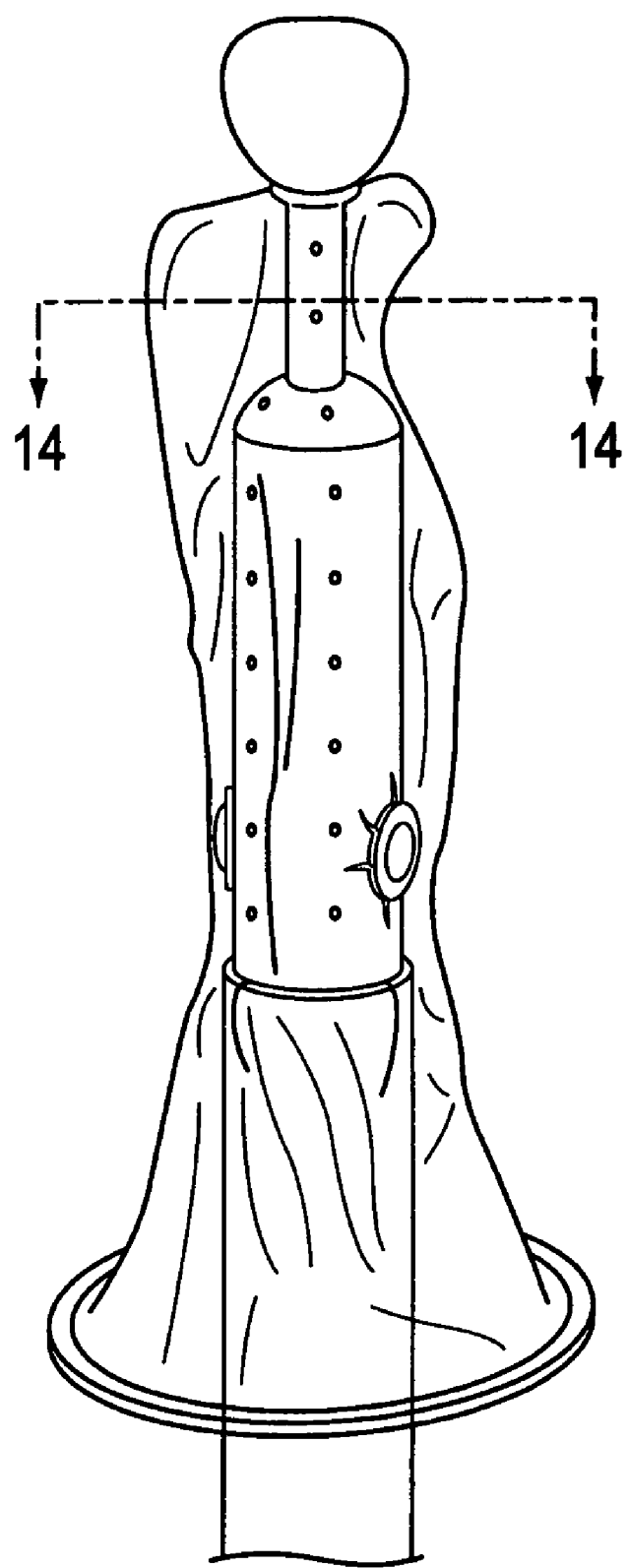
FIG. 12 is an elevational view of the female condom of FIG. 7 with vertical pleats formed according to another embodiment of the invention.

FIG. 9 shows a cross section of female condom 1", collapsed on mandrel 50 by vacuum pressure, with four vertical pleats 24 formed. FIG. 9 corresponds generally to FIG. 8. FIG. 11 shows a cross section of a female condom collapsed into an end cap (such as cap 20"), showing a preferable configuration of alternately folded and packed pleats of pouch material (such as pouch 10") and cling elements (such as cling elements 15").

Steps for using a mandrel to collapse the inventive female condom into its cap, in such a manner as to allow easy insertion and deployment, are described below as one example of a procedure to collapse the condom:

1. Clean mandrel and handling surfaces.
2. Attach vacuum source to mandrel.
3. Raise vacuum slide to cover bottom 3 holes.
4. Adjust vacuum to ≈0.25 inch-0.5 inch Hg.
5. Drape condom over mandrel with cap reversed (i.e., turned wholly or partly inside out).
6. Arrange vertical pleats and foam cling elements to alternate (see e.g., FIG. 9).
7. Grasp condom at cling elements to trap vacuum and thereby evacuate space in the condom above the grasping hand.
8. Adjust pleats as needed.
9. Slide condom up the mandrel piling pleats/wrinkles ahead of hand (see e.g., FIG. 10).
10. Slide vacuum slide up as necessary cover holes exposed as hand moves upward, so as to maintain 1 inch-3 inch Hg.
11. When you reach the necked-down portion, grasp the bunched pouch in your gripping hand to compress it.
12. With free hand, pull cap and push bunched pouch off mandrel.
13. Hold bunched pouch together while turning the cap right-side-out over the bunched pouch.

14. Push the bunched pouch up into the cap while gently pulling back the pouch material between the inserted foam retention elements and the open end.

The above sequence is only an example. Various steps may be modified, rearranged or deleted, and/or other steps added. Additionally, such a process may be automated for ease of manufacture.

Figure 13:
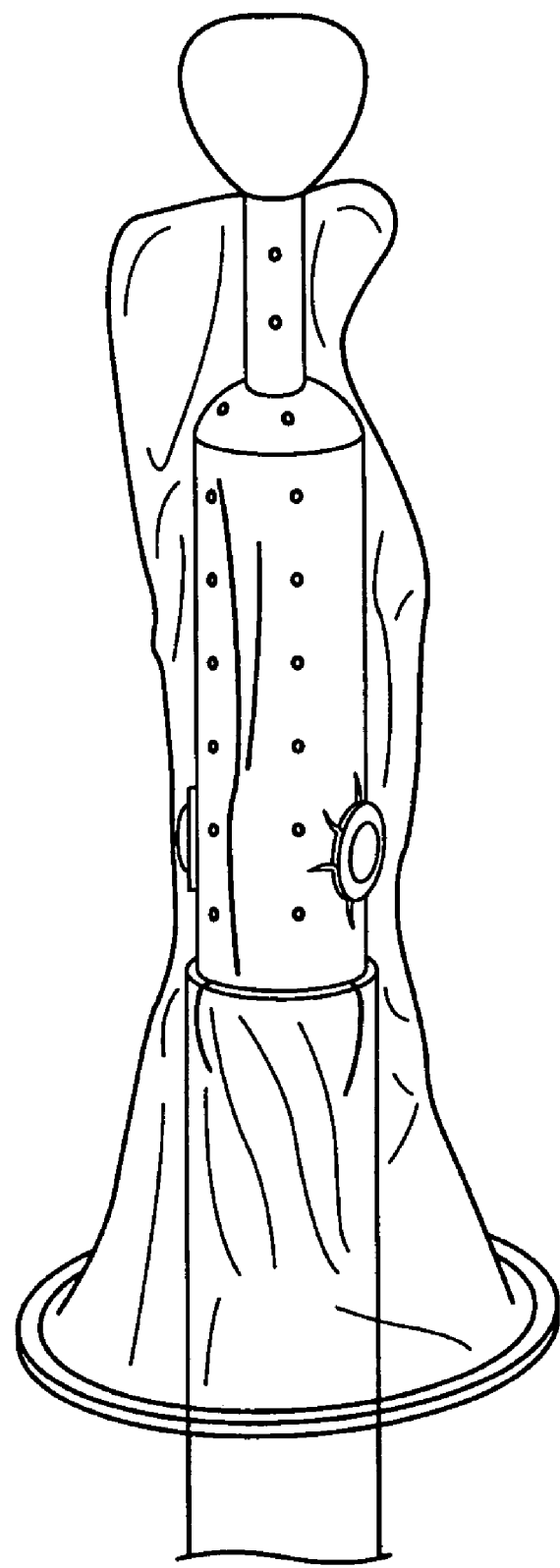
FIG. 13 is another elevational view of the embodiment of FIG. 12.
Figure 14:
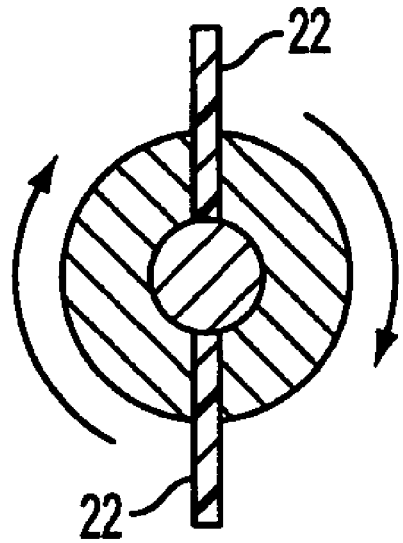
FIG. 14 is a cross-sectional view through the female condom with vertical pleats of FIGS. 12 and 13 at the neck portion of the mandrel.
Figure 15:
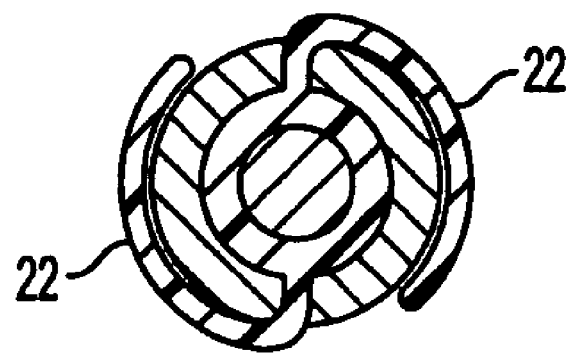
FIG. 15 shows folding the pleats of FIGS. 12 and 13 from the cross-sectional view of FIG. 14.
Figure 16:
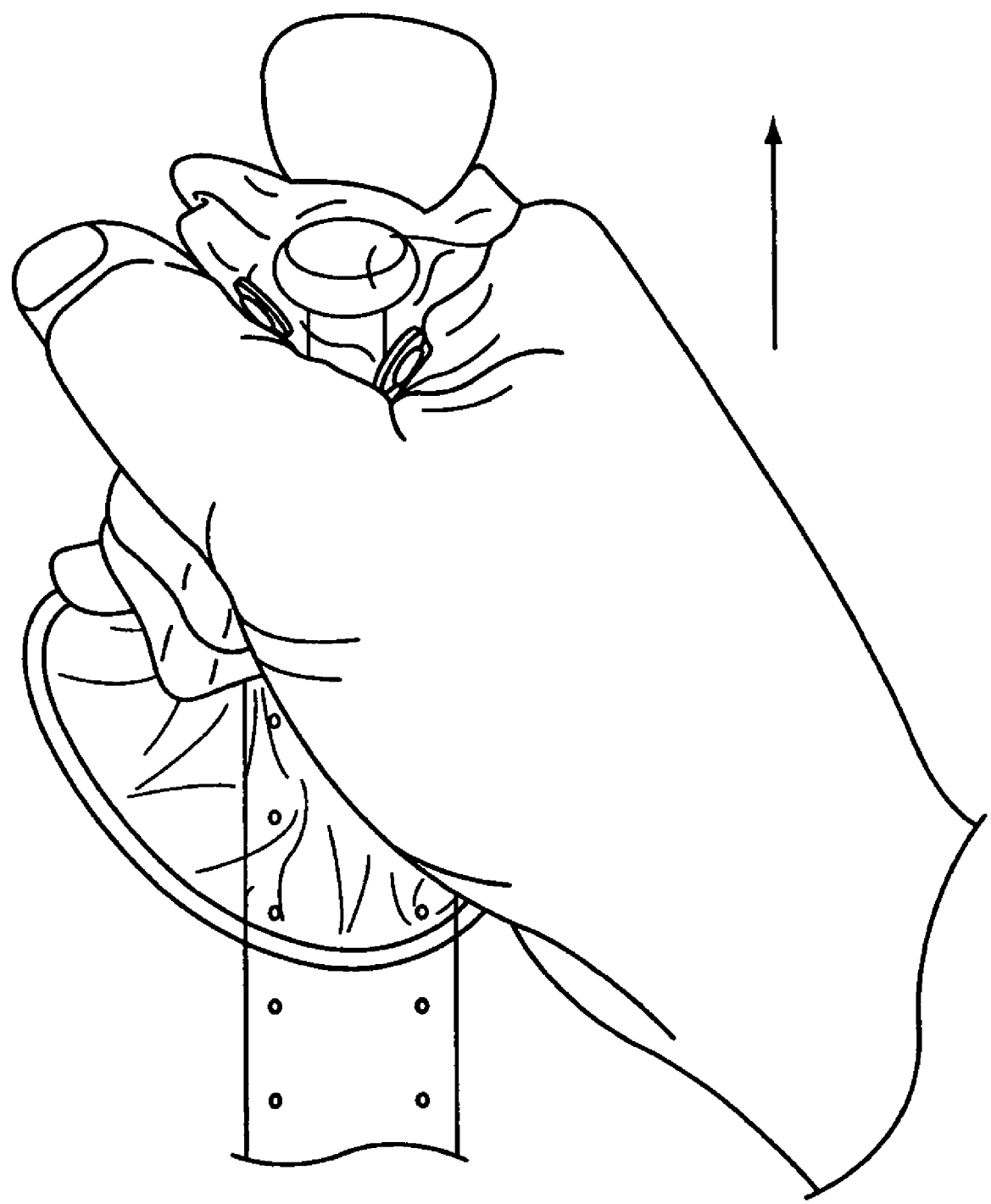
FIG. 16 is a perspective view of the condom and mandrel of FIGS. 12 and 13 illustrating collapsing a female condom according to the embodiment of FIGS. 12 and 13.

Referring now to FIGS. 12-15, a method for collapsing and compressing the pouch of female condom, such as female condom 1", according to another embodiment of the invention is generally shown. Aspects and preferences for this embodiment are generally the same as for the embodiment of FIGS. 7-11, except that two pleats 22 are formed as opposed to four pleats 24 as discussed above. FIG. 14 shows a cross section of female condom 1" according to the invention when collapsed on mandrel 50 after application of vacuum pressure. The cross section of FIG. 14 corresponds generally to the necked down portion of the mandrel shown in FIG. 12, and shows two vertical pleats 22. As shown in FIG. 15, vertical pleats 22 may then be wrapped around mandrel 50. Condom 1" may then be collapsed upward as shown in FIG. 16.

Figure 17:
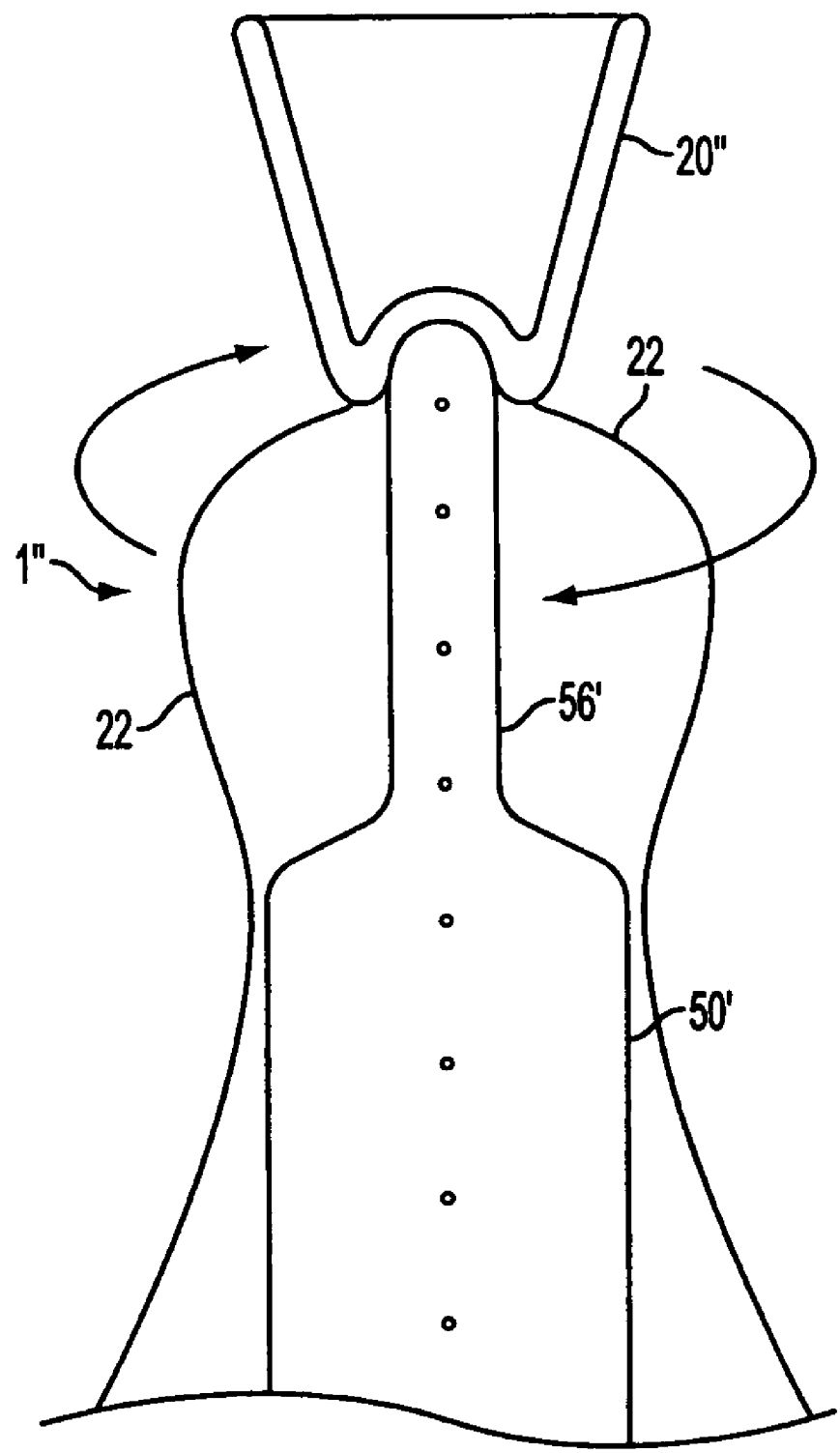
FIG. 17 shows a female condom disposed on a mandrel according to a further embodiment of the invention.

Referring now to FIG. 17, an alternative device for collapsing and compressing the pouch of a female condom, such as condom 1", is generally shown according to a further embodiment of the invention. The mandrel 50' shown in FIG. 13 is similar to that of FIG. 7, except that a lip is not formed on the upper end 56.

Figure 18:
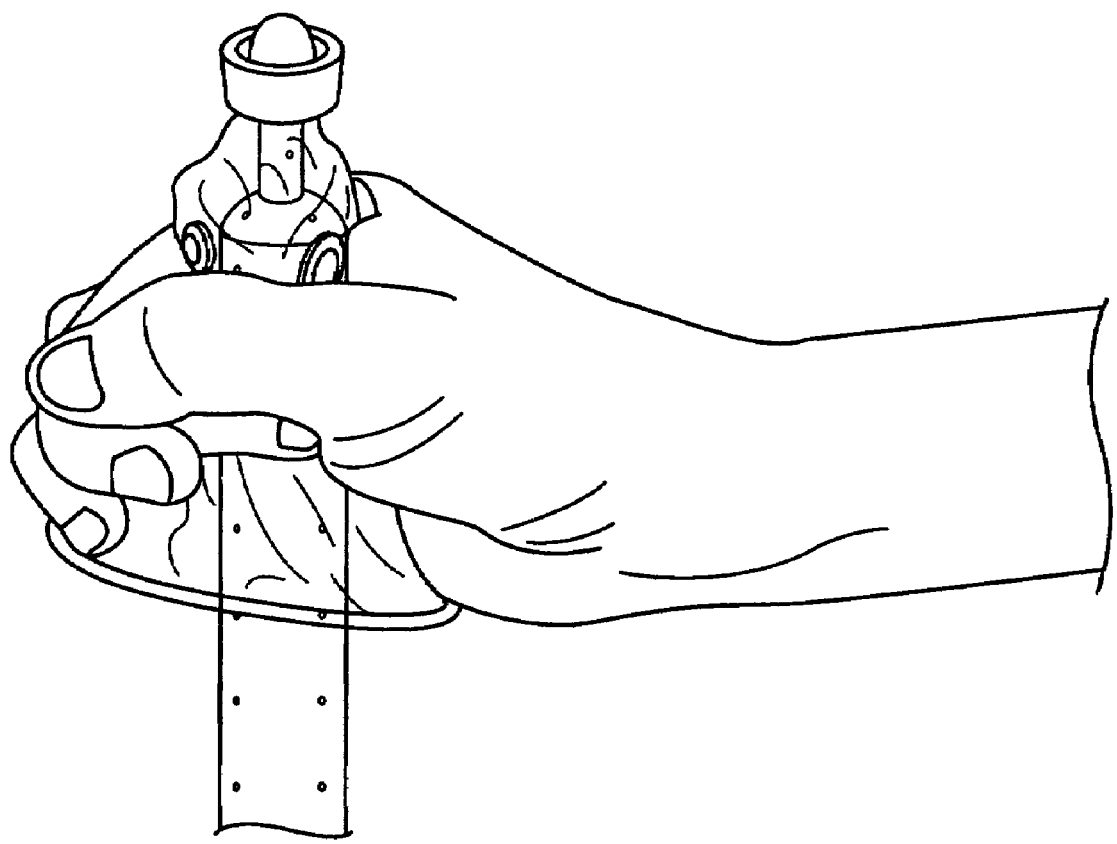
FIG. 18 shows a female condom disposed on a mandrel for packaging the condom according to yet another embodiment of the invention.

Referring now to FIG. 18, an alternate method of packing the pouch into the cap is generally shown according to yet another embodiment of the invention. Aspects and preferences for this embodiment are generally the same as for the embodiment of FIGS. 7-11, except as related to folding end cap 20. In this alternate method, the end cap 20 is not completely reversed (i.e., not turned completely inside out), but is instead "cuffed" by turning up the lower edge of the end cap. The method is otherwise similar to that described above with FIGS. 7-11.

Figure 19:
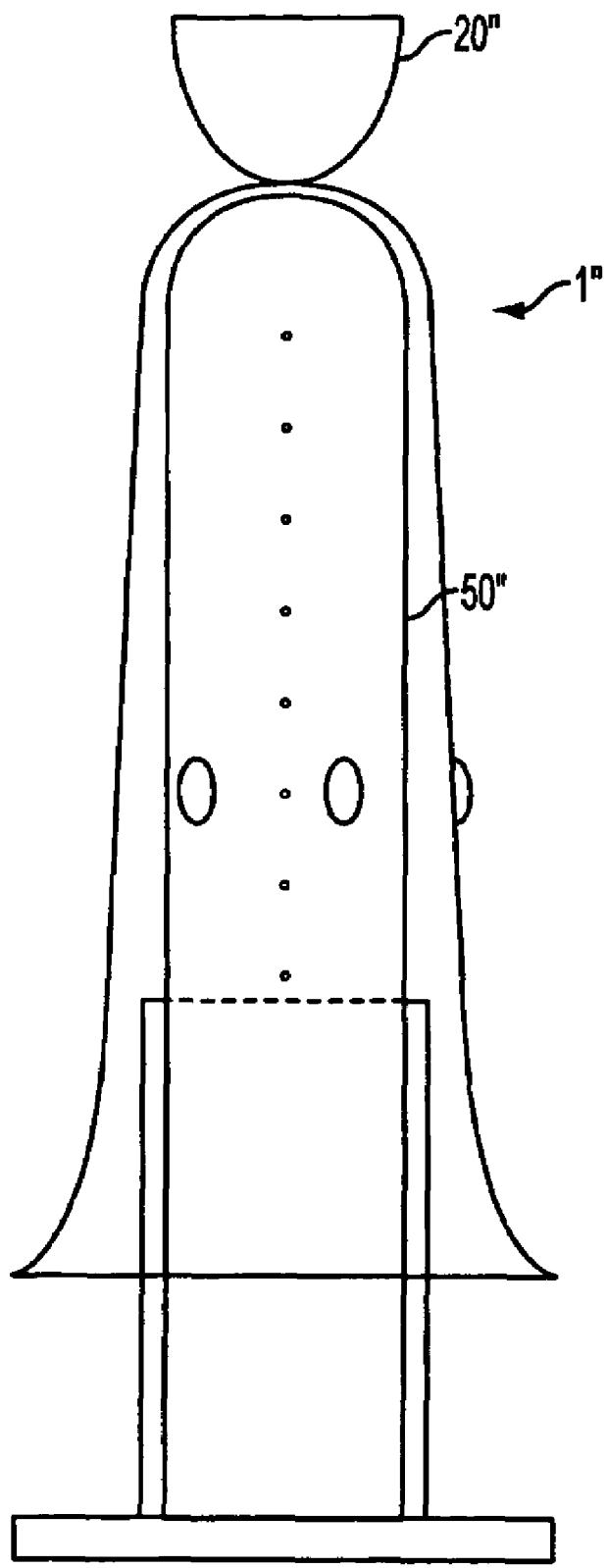
FIG. 19 is an elevational view of a female condom disposed on a mandrel according to an additional embodiment of the invention.

Referring now to FIG. 19, another alternative device for collapsing and compressing the pouch is generally shown according to an additional embodiment of the invention. The mandrel 50" shown in FIG. 19 is similar to that of FIGS. 7 and 17, except that the upper portion is not necked down and has no lip formed thereon. The tip of the mandrel 50" may be hemispherical.

It will be understood that while the invention has been described in conjunction with various embodiments thereof, the foregoing description and examples are intended to illustrate, but not limit the scope of the invention. Other variations may be made without departing from the true spirit and scope of the invention. For example, modifications upon materials, dimensions and steps are within the scope of the invention.

We claim:

1. A female condom, comprising:
    a pouch of resilient membranous material having an open end, a closed end, an outer surface and an inner surface;
    at least one hydrophilic cling element attached to said outer surface of said pouch, said at least one cling element being disposed between said open end and said closed end, each one of said cling elements adapted to cling lightly to walls of a vagina proximate a transition zone between the vagina's introitus and its rugated internal vaginal tissue for anchoring said pouch in or slightly beyond said introitus; and
    an inserter attached to said pouch for retaining a distal portion of said pouch and facilitating insertion of said female condom into a vagina;
    wherein said inserter is generally dissolvable in the vaginal environment and said distal portion of said pouch is slidably retained in said inserter.

2. The female condom of claim 1, wherein said female condom includes at least three hydrophilic cling elements.

3. The female condom of claim 2, wherein said at least three hydrophilic cling elements includes four foam cling elements to six foam cling elements.

4. The female condom of claim 2, wherein said hydrophilic cling elements are disposed in a belt-like pattern around said pouch.

5. The female condom of claim 1, wherein at least one hydrophilic cling element defines a generally elliptical shape.

6. The female condom of claim 1, wherein said at least one hydrophilic cling element defines a shape selected from the group consisting of a generally triangular shape and a generally circular shape.

7. The female condom of claim 1, wherein said at least one hydrophilic cling element is a polyurethane hydrophilic foam segment.

8. The female condom of claim 1, wherein said at least one hydrophilic cling element has a total surface area of approximately 0.75 square inches.

9. The female condom of claim 1, wherein said inserter is a cap attached to said pouch.

10. The female condom of claim 9, wherein said cap is selected from the group consisting of an elastomeric cap and a foam cap.

11. The female condom of claim 1, wherein a distal portion of said pouch is packed inside of said inserter.

12. The female condom of claim 11, wherein said at least one hydrophilic cling element is packed inside of said inserter.

13. The female condom of claim 1, wherein said inserter is selected from the group consisting of a band, a capsule, a spherical inserter, a envelope-shaped inserter, a bullet-tipped cylindrical inserter, and a closed-ended pouch.

14. The female condom of claim 1, wherein said inserter comprises a water-soluble material.

15. The female condom of claim 14, wherein said water-soluble material includes polyvinyl alcohol.

16. The female condom of claim 1, wherein the at least one hydrophilic cling element is welded to the outer surface of the pouch.

17. The female condom of claim 1, wherein the at least one hydrophilic cling element is disposed 3 inches to 4 inches from said open end.

18. A female condom, comprising:
    an elongated pouch of resilient membranous material having an open end, a closed end, an outer surface, an inner surface and a longitudinal axis; and
    a cling mechanism attached to said outer surface of said pouch and disposed between said open end and said closed end, said cling mechanism adhering to said pouch without imparting outward biasing force thereto; and
    an inserter attached to said pouch for retaining a distal portion of said pouch and facilitating insertion of said female condom into a user's vagina;
    wherein said inserter is generally dissolvable in the vaginal environment and, upon insertion into a user's vagina, said cling mechanism comes into contact with vaginal walls proximate a transition zone between the vagina's introitus and its rugated internal vaginal tissue, and clings lightly to the vaginal walls.

19. The female condom of claim 18, wherein said cling mechanism comprises a plurality of hydrophilic foam elements.

20. The female condom of claim 18, wherein said cling mechanism being disposed in a belt-like pattern generally about said longitudinal axis.

21. The female condom of claim 20, wherein each said hydrophilic foam element defines selected from the group consisting of a generally elliptical shape, a generally triangular shape and a generally circular.

22. The female condom of claim 18, wherein the cling mechanism is welded to the outer surface of the pouch.

23. The female condom of claim 18, wherein the cling mechanism is disposed 3 inches to 4 inches from said open end.

24. A packaged female condom comprising:
a pouch having an open end and a distal end; and
an inserter attached to said distal end of the pouch, said inserter retaining a distal portion of said pouch in a collapsed form;
wherein said inserter is generally dissolvable in the vaginal environment.

25. The female condom package of claim 24, further comprising:
a cling mechanism attached to an outer surface of said pouch and disposed between said open end and said distal end of said pouch, said cling mechanism including a hydrophilic foam cling element;
wherein said inserter retains said cling mechanism in a collapsed form and, upon insertion into a user's vagina, said cling mechanism deploys from said inserter and comes into contact with vaginal walls for lightly clinging to said vaginal walls.

26. The female condom package of claim 24, further comprising a plurality of first pleats formed in a distal portion of said pouch.

27. The female condom package of claim 26, further comprising a plurality of second pleats formed in said distal portion of said pouch, said second pleats being disposed generally perpendicular to said first pleats.

28. The female condom package of claim 24, wherein said inserter is a selected from the group consisting of an elastomeric cap and a foam cap.

29. The female condom package of claim 24, wherein said dissolvable inserter is selected from the group consisting of a band, a capsule, a spherical inserter, a envelope-shaped inserter, a bullet-tipped cylindrical inserter, and a closed-ended pouch.

30. The packaged female condom of claim 24, wherein the cling mechanism is welded to the outer surface of the pouch.

31. The packaged female condom of claim 25, wherein the cling mechanism is disposed 3 inches to 4 inches from said open end.

32. A method for packaging a female condom, said female condom comprising an elongated pouch having an open portion and an opposite distal portion, said pouch defining an inner cavity, said method comprising:
forming a plurality of longitudinal pleats in said distal portion of said pouch wherein said longitudinal pleats are disposed generally parallel to a longitudinal axis of said pouch;
folding said longitudinal pleats generally parallel to said longitudinal axis wherein said longitudinal pleats overlap said distal portion;
collapsing said distal portion of said pouch in a direction generally parallel to said longitudinal axis toward a distal end and forming lateral pleats in said distal portion, wherein said lateral pleats are disposed generally perpendicular to said longitudinal axis; and
placing an inserter about said collapsed distal portion.

33. The method of claim 32, wherein the step of forming a plurality of longitudinal pleats compnses:
placing said pouch over an elongated mandrel wherein a portion of said mandrel is disposed within said pouch inner cavity;
withdrawing air from said inner cavity wherein at least said distal portion of said pouch collapses about said mandrel; and
arranging said longitudinal pleats in said pouch.

34. The method of claim 33, wherein the step of arranging comprises forming each of said pleats between an adjacent pair of cling elements attached to an outer side of said pouch;
and wherein the step of folding comprises rotating each of said longitudinal pleats in one of a clockwise direction and a counter-clockwise direction generally about said longitudinal axis;
and wherein the step of forming lateral pleats comprises sliding said distal portion about a mandrel disposed within said inner cavity;
and wherein the step of placing an inserter about said collapsed distal portion comprises turning at least a portion of a cap inside-out to retain said distal portion.

* * * * *